US006428802B1

(12) United States Patent
Atala

(10) Patent No.: US 6,428,802 B1
(45) Date of Patent: Aug. 6, 2002

(54) PREPARING ARTIFICIAL ORGANS BY FORMING POLYLAYERS OF DIFFERENT CELL POPULATIONS ON A SUBSTRATE

(75) Inventor: Anthony Atala, Weston, MA (US)

(73) Assignee: Children's Medical Center Corp., Boston, MA (US)

( * ) Notice: Subject to any disclaimer, the term of this patent is extended or adjusted under 35 U.S.C. 154(b) by 0 days.

(21) Appl. No.: 09/474,524

(22) Filed: Dec. 29, 1999

(51) Int. Cl.[7] .......................... A61F 2/00; C12N 11/02; C12N 11/08; C12N 5/06; C12N 5/08

(52) U.S. Cl. ...................... 424/423; 424/93.7; 425/177; 425/180; 425/395

(58) Field of Search ................................ 435/177, 180, 435/395; 424/423, 93.7

(56) References Cited

U.S. PATENT DOCUMENTS

| | | | |
|---|---|---|---|
| 4,458,678 A | 7/1984 | Yannas et al. | 128/155 |
| 4,520,821 A | 6/1985 | Schmidt et al. | 128/334 |
| 4,963,489 A | 10/1990 | Naughton et al. | 435/240.1 |
| 4,996,154 A | * 2/1991 | Gabriels, Jr. | 435/350 |
| 5,032,508 A | 7/1991 | Naughton et al. | 435/32 |
| 5,160,490 A | 11/1992 | Naughton et al. | 435/284 |
| 5,443,950 A | 8/1995 | Naughton et al. | 435/1 |
| 5,516,680 A | 5/1996 | Naughton et al. | 435/240.243 |
| 5,567,612 A | 10/1996 | Vacanti et al. | 435/240.23 |
| 5,753,267 A | 5/1998 | Badylak et al. | 424/551 |
| 5,759,830 A | 6/1998 | Vacanti et al. | 435/180 |
| 5,762,966 A | 6/1998 | Knapp, Jr. et al. | 424/551 |
| 5,770,193 A | 6/1998 | Vacanti et al. | 424/93.7 |
| 5,770,417 A | 6/1998 | Vacanti et al. | 435/180 |
| 5,800,537 A | * 9/1998 | Bell | 623/11 |
| 5,851,833 A | 12/1998 | Atala | 435/378 |
| 5,855,610 A | 1/1999 | Vacanti et al. | 623/11 |
| 5,858,721 A | 1/1999 | Naughton et al. | 435/69.1 |
| 5,863,531 A | 1/1999 | Naughton et al. | 424/93.7 |
| 5,866,414 A | 2/1999 | Badylak et al. | 435/325 |
| 5,916,265 A | 6/1999 | Hu | 623/11 |
| 5,962,325 A | 10/1999 | Naughton et al. | 435/395 |
| 6,140,039 A | * 10/2000 | Naughton et al. | 435/1.1 |

FOREIGN PATENT DOCUMENTS

| | | |
|---|---|---|
| WO | 8803785 | 6/1988 |
| WO | 8901967 | 3/1989 |
| WO | WO 93/07913 | 4/1993 |
| WO | WO 96/40175 | 12/1996 |
| WO | WO 98/06445 | 2/1998 |
| WO | 9809582 | 3/1998 |
| WO | WO 99/22781 | 5/1999 |

OTHER PUBLICATIONS

International Search Report, PCT/US00/33811, issued Apr. 2, 2001.
Atala, A., "Tissue Engineering for Bladder Substitution", *World J. Urol.*, vol. 18: 364–370 (2000).
Oberpenning, F., "De Novo Reconstitution of a Functional Mammalian Urinry Bladder by Tissue Engineering", *Nature Biotechnology*, vol. 17: 149–155 (Feb., 1999).
Atala, A. et al., "Formation of Urothelial Structures in Vivo From Dissociated Cells Attached to Biodegradable Polymer Scaffolds in Vitro," *The Journal of Urology*, vol. 148, 658–62 (Aug. 1992).
Atala, A. et al., "Implantation in Vivo and Retrieval of Artificial Structures Consisting of Rabbit and Human Urothelium and Human Bladder Muscle," *The Journal of Urology*, vol. 150, 608–12 (Aug. 1993).
Atala, A. et al., "Injectable Alginate Seeded with Chondrocytes as a Potential Treatment for Vesicoureteral Reflux," *The Journal of Urology*, vol. 150, 745–7 (Aug. 1993).
Ben–Ze'ev, A. et al., "Cell–cell and Cell–matrix Interactions Differentially Regulate the Expression of Hepatic and Cytoskeletal Genes in Primary Cultures of Rat Hepatocytes," *PNAS*, vol. 85, 2161–5 (Apr. 1988).
Bissell, D. et al., "Interactions of Rat Hepatocytes with Type IV Collagen, Fibronectin and Laminin Matrices. Distinct Matrix–controlled Modes of Attachment and Spreading," *European Journal of Cell Biology*, vol. 40, 72–8 (1986).
Burke, J., "The Effects of the Configuration of an Artificial Extracellular Matrix on the Development of a Functional Dermis," *The Role Extracellular Matrix in Development*, Alan R. Liss, Inc., eds. (NY), 351–55 (1984).
Cilento, B. et al., "Phenotypic and Cytogenetic Characterization of Human Bladder Urothelia Expanded in Vitro," *The Journal of Urology*, vol. 152, 665–70 (Aug. 1994).
Culliton, B., "Gore Tex Organoids and Genetic Drugs," *Science*, vol. 246, 747–9 (Nov., 10, 1989).
Davis, G. et al., "Human Amnion Membrane Serves as a Substratum for Growing Axons in Vitro and in Vivo," *Science*, vol. 236, 1106–9 (May 29, 1987).
Ebata, H. et al., "Liver Regeneration Utilizing Isolated Hepatocytes Transplanted into the Rat Spleen," *Surg Forum*, vol. 29, 338–40 (1978).
Fontaine, M. et al., "Transplantation of Genetically Altered Hepatocytes Using Cell–Polymer Constructs," *Transplantation Proceedings*, vol. 25, No. 1, 1002–4 (Feb. 1993).

(List continued on next page.)

*Primary Examiner*—David M. Naff
(74) *Attorney, Agent, or Firm*—Thomas Engellenner; Jasbir Sagoo; Nutter, McClennen & Fish, LLP

(57) ABSTRACT

Compositions and methods are provided for producing multilayered artificial organs comprising heterogenous polylayers. Polylayers comprising homogenous cell populations are created on one side of a biocompatible substrate such that a chimeric interface is produced between the heterogenous polylayers. Cellular interaction at the chimeric interface produce an interstitial biomaterial with morphological and functional characteristics that resemble the natural in vivo organ. An artificial organ is produced by creating a first cultured polylayer of cells derived from an isolated population of smooth muscle cells on a substrate in the shape of an organ, and creating a second cultured polylayer of cells derived from a cell population different from the smooth muscle cell population.

31 Claims, No Drawings

OTHER PUBLICATIONS

Gilbert, J. et al., "Cell Transplantation of Genetically Altered Cells on Biodegradable Polymer Scaffolds in Syngeneic Rats," *Transplantation*, vol. 56, No. 2, 423–7 (Aug. 1993).

Henry, E. W. et al., "Nerve Regeneration Through Biodegradable Polyester Tubes," *Experimental Neurology*, vol. 90, 652–76 (1985).

Humes, H. D. et al., "Replacement of Renal Function in Uremic Animals With a Tissue–Engineered Kidney," *Nature Biotechnology*, vol. 17, 451–5 (May 1999).

Ingber, D. et al., "Endothelial Growth Factors and Extracellular Matrix Regulate DNA Synthesis Through Modulation of Cell and Nuclear Expansion," *In Vitro Cellular & Developmental Biology*, vol. 23, No. 5, 387–94 (May 1987).

Jauregui, H. O. et al., "Attachment and Long Term Survival of Adult Rat Hepatocytes in Primary Monolayer Cultures: Comparison of Different Substrata and Tissue Culture Media Formulations," *In Vitro Cellular & Developmental Biology*, vol. 22, No. 1, 13–22 (Jan. 1986).

Langer, R. and Moses, M., "Biocompatible Controlled Release Polymers for Delivery of Polypeptides and Growth Factors," *Journal of Cellular Biochemistry*, vol. 45, 340–5 (1991).

Michalopoulos, G. and Pitot, H. C., "Primary Culture of Parenchymal Liver Cells on Collagen Membranes," *Experimental Cell Research*, vol. 94, 70–8 (1975).

Mooney, D. and Vacanti, J., "Tissue Engineering Using Cells and Synthetic Polymers," *Transplantation Reniews*, vol. 7, No. 3, 153–62 (Jul. 1993).

Naughton, B. et al., "Long–term Growth of Rat Bone Marrow Cells in a Three–dimensional Matrix," *The Anatomical Record*, vol. 218, 97A (1987).

Nikolovski, J. et al., "Design Engineering of a Bioartificial Renal Tubule Cell Therapy Device," *Cell Transportation*, vol. 8, 351–64 (1999).

O'Connor, N. et al., "Grafting of Burns with Cultured Epithelium Prepared from Autologous Epidermal Cells," *The Lancet*, 75–8 (Jan. 10, 1981).

Puelacher, W. C. et al., "Tissue–engineered Growth of Cartilage: The Effect of Varying the Concentration of Chondrocytes Seeded Onto Synthetic Polymer Matrices," *Int. J. Oral Maxillofac. Surg.*, vol. 23, 49–53 (1994).

Reid, L. et al., "Long–term Cultures of Normal Rat Hepatocytes on Liver Biomatrix," *Annals New York Academy of Sciences*, 70–6 (1980).

Rhine, W. et al., "Polymers for Sustained Macromolecule Release: Procedures to Fabricate Reproducible Delivery Systems and Control Release Kinetics," *Journal of Pharmaceutical Sciences*, vol. 69, No. 3, 265–70 (Mar. 1980).

Rosen, H. B. et al., "Bioerodible Polyanhydrides for Controlled Drug Delivery," *Biomaterials*, vol. 4, 131–3 (Apr. 1983).

Sawada, N. et al., "Effects of Extracellular Matrix Components on the Growth and Differentiation of Cultured Rat Hepatocytes," *In Vitro Cellular & Developmental Biology*, vol. 23, No. 4, 267–73 (Apr. 1987).

Seckel, B. R. et al., "Nerve Regeneration Through Synthetic Biodegradable Nerve Guides: Regulation by the Target Organ," *Plastic and Reconstructive Surgery*, vol. 74, No. 2, 173–81 (Aug. 1984).

Shine, H. D. et al., "Cultured Peripheral Nervous System Cells Support Peripheral Nerve Regeneration Through Tubes in the Absence of Distal Nerve Stump," *Journal of Neuroscience Research*, vol. 14, 393–401 (1985).

da Sliva, C. et al., "An In Vivo Model to Quantify Motor and Sensory Peripheral Nerve Regeneration Using Bioresorbable Nerve Guide Tubes," *Brain Research*, vol. 342, 307–15 (1985).

Tachibana, M. et al., "Ureteral Replacement Using Collagen Sponge Tube Grafts," *The Journal of Urology*, vol. 133, 866–9 (May 1985).

Takeda, T. et al., "Hepatocyte Transplantation in Biodegradable Polymer Scaffolds Using the Dalmation Dog Model of Hyperuricosuria," Transplantation Proceedings, vol. 27, No. 1, 635–6 (Feb 1995).

Thompson, J. et al., "Heparin–binding Growth Factor 1 Induces the Formation of Organoid Neovascular Structures in vivo," *PNAS*, vol. 86, 7928–32 (Oct. 1989).

Thompson, J. A. et al., "Implantable Bioreactors: Modern Concepts of Gene Therapy," *Current Communications in Molecular Biology: Therapeutic Peptides and Proteins*, Cold Spring Harbor Laboratory, eds., 143–7 (1989).

Urry, D. and Pattanaik, A., "Elastic Protein–based Materials in Tissue Reconstruction," *Annals New York Academy of Sciences*, vol. 831,32–46 (Dec. 31, 1997).

Uyama, S. et al., "Delivery of Whole Liver–equivalent Hepatocyte Mass Using Polymer Devices and Hepatotrophic Stimulation," *Transplantation*, vol. 55, No. 4, 932–5 (Apr. 1993).

Walton, R. and Brown, R., "Tissue Engineering of Biomaterials for Composite Reconstruction: an Experimental Model," *Annals of Plastic Surgery*, vol. 30, No. 2, 105–10 (Feb. 1993).

* cited by examiner

PREPARING ARTIFICIAL ORGANS BY FORMING POLYLAYERS OF DIFFERENT CELL POPULATIONS ON A SUBSTRATE

BACKGROUND OF THE INVENTION

The technical field of this invention is the creation of artificial organs in vitro with subsequent implantation of the artificial organ in vivo, and in particular to the creation of multilayered cellular organs with a natural interface between the tissue layers.

A considerable amount of effort from the medical community is directed to substitution of defective organs with replacements of the entire organ or a part of the organ. In many instances these organs are completely synthetic, such as artificial hearts, or completely natural, such as organs from mammalian donors. However, there are limitations with both approaches. With natural organ transplants there is the potential risk for transmission of diseases like AIDS and hepatitis, or rejection of the transplanted organ. In addition, the availability of a donor organ is often a rate limiting factor. With synthetic organs there are complications associated with the formation of mechanical failure and calculus formation.

Several approaches have been explored for reconstruction of defective organs and tissues. Initially, the feasibility of cell survival was demonstrated by injecting suspensions of dissociated cells into other tissues such as fat, liver or, with the stroma of the host tissue providing the matrix for cell attachment and reorganization. However, a sustained increase in cell mass was not observed, thus underscoring the limitations of trying to achieve growth and structuring of new tissue in pre-existing tissue (See Cima, et al., (1991) *J. Biomech. Engr.*, 113:143–151).

Alternatively, organs have been prepared on various matrices. The cellular morphology and metabolic activity of cultured cells are affected by the composition of the matrix on which they are grown. Presumably cultured cells function best (i.e. proliferate and perform their natural in vivo functions) when cultured on matrices that closely mimic their natural environment. Currently, in vitro studies of cellular function are limited by the availability of cell growth matrices that present the appropriate physiological environment for proliferation and development of the cultured cells.

A further limitation in organ reconstruction has been mimicking the cellular organization of a multilayered organ. Many organs are made up of multiple layers of different tissues. Depending on the functional role of the organ, different tissues confer different properties to the organ. For example, the bladder has three main layers of tissue: the mucosa, submucosa and detrusor. The mucosa, comprising urothelial cells, is the innermost layer and is composed of transitional cell epithelium. The submucosa lies immediately beneath the mucosa and its basement membrane. It is a layer of interstitial protein that supports blood vessels, which supply the mucosa with nutrients and the lymph nodes which aid in the removal of waste products. The submucosa serves an important function, and is produced at the interface between the mucosa and the detrusor. The detrusor is a layer of smooth muscle cells which expands to store urine and contracts to expel urine. Natural interfaces produced in vivo between different cell populations result in the formation of several biological features that have important structural and functional properties, for example the production of the submucosa which supplies nutrients to the mucosa.

Reconstruction of multilayered organs has typically involved coating both sides of a matrix with different cell populations. In these instances, the matrix functions as an artificial barrier between the different cell populations (See Atala et al. U.S. Ser. No. 60/063,790, filed Oct. 31, 1997, entitled "Bladder Reconstruction"). Although some interactions occur between the two different cell populations through the pores of the matrix, these interactions, are at best, minimal, and lack the cell-cell interactions characteristic of whole tissue in vivo. This prevents normal functional and morphological interactions which result in the formation of biological material, such as epithelial cells, like, bladder submucosa, oral mucosa and nasal epithelium. The presence of the submucosa provides growth factors and other proteins which promote normal division and differentiation.

Therefore, there exists a need to create artificial organs that have natural interfaces between different cell populations, to produce artificial organs that more closely resemble the interface of native in vivo organs.

SUMMARY OF THE INVENTION

It is the object of the invention to provide artificial organs with a chimeric interface between two different cell populations that more closely resembles the interface of a native in vivo organ.

It is the object of the invention to provide methods of producing artificial organs with a chimeric interface between two different cell populations that more closely resembles the interface of a native in vivo organ.

It is the object of the invention to provide artificial organs in which cells retain their normal morphology and cell function.

The invention is based, in part, on the discovery that growth of a different population of cells on biocompatible substrate with a chimeric interface between the different cell populations produces new interstitial biomaterial that resembles the equivalent biomaterial in a native in vivo organ. This can be accomplished by sustaining active proliferation of heterogenous polylayers comprising different populations of cells in culture, such that each polylayer resembles the equivalent parenchyma tissue of an in vivo organ. This may be due, in part, by the method of producing the polylayers. Polylayers are produced by culturing a first homogenous cell population one layer at a time on the biocompatible substrate until the cells of each layer are actively proliferating. The polylayers are incubated until the cells develop and proliferate to resemble the structure and morphology of the equivalent parenchyma tissue of an in vivo organ.

Polylayers developed by the method of the invention therefore produce proteins, growth factors and regulatory factors necessary to support the long term proliferation of the homogenous cell population. After the first polylayer has been established, this provides the surface for producing the second polylayer. The second polylayer comprises a second homogenous cell population that is different from the first homogenous cell population. The second polylayer is developed by culturing the second homogenous cell population one layer at a time until the cells of each layer are actively proliferating to produce a polylayer of cells.

A chimeric interface is produced where the cells of the two polylayers are in contact. This creates a cellular microenvironment that is analogous to that of an in vivo multicellular organ. By creating such a microenvironment, the cells at the interface proliferate, differentiate and segregate as they would in vivo, unhindered by any structural constraints. This also allows the cells at the interface to resume a more natural morphology, structure, and spatial distribution, which more closely approximates conditions in vivo. The growth of cells at the chimeric interface may be further enhanced by adding proteins, glycoproteins, glycosaminoglycans, a cellular matrix, and other materials between the different polylayers.

Accordingly, in one aspect, the invention features an artificial organ construct comprising:

a first cultured polylayer of cells derived from a first cell population; and a second cultured polylayer of cells derived from a second cell population that is different from the first cell population, wherein the second polylayer is coupled to the first polylayer by a chimeric interface such that the construct provides the functional equivalent of a natural biological structure upon implantation.

In one embodiment, the artificial organ further comprises a third cultured polylayer of cells derived from a third cell population that is different from the first cell population and the second cell population, wherein the third polylayer is coupled to the second polylayer by a chimeric interface.

In a preferred embodiment, the chimeric interface further comprises an interstitial biomaterial produced by at least one of the polylayers. The interstitial biomaterial comprises cells with a normal morphology.

In another embodiment, the artificial organ further comprises factors layered between the first and second polylayers, wherein the factors are selected from the group consisting of nutrients, growth factors, cytokines, extracellular matrix components, inducers of differentiation, products of secretion, immunomodulators, biologically-active compounds which enhance or allow growth of the cellular network or nerve fibers.

In one embodiment, the artificial organ is selected from the group consisting of heart, kidney, liver, pancreas, spleen, bladder, ureter and urethra. In another embodiment, the artificial organ is part of an organ selected from the group consisting of heart, kidney, liver, pancreas, spleen, bladder, ureter and urethra.

In another aspect, the invention features an artificial bladder construct comprising:

a first cultured polylayer of cells derived from a smooth muscle cell population; and a second cultured polylayer of cells derived from a urothelial cell population, wherein the second polylayer is coupled to the first polylayer by a chimeric interface such that the construct provides the functional equivalent of a natural bladder upon implantation.

In a preferred embodiment, the chimeric interface further comprises an interstitial submucosa produced by at least one of the polylayers.

In another aspect, the invention features a method for producing an artificial organ construct comprising:

providing a biocompatible substrate in the shape of an organ;

creating a first cultured polylayer of cells derived from a first cell population on one area of the biocompatible substrate, wherein the first polylayer is attached to the biocompatible substrate;

creating a second cultured polylayer of cells derived from a second cell population that is different from the first cell population, wherein the second polylayer is coupled to the first polylayer by a chimeric interface such that the construct provides the functional equivalent of a natural biological structure upon implantation, thereby producing an artificial organ construct.

In one embodiment, the biocompatible substrate is a polymer. In another embodiment, the biocompatible substrate is a decellularized organ. In one embodiment, the decellularized organ is selected from the group consisting of heart, kidney, liver, pancreas, spleen, bladder, ureter and urethra. In another embodiment, the decellularized organ is a part of a decellularized organ selected from the group consisting of heart, kidney, liver, pancreas, spleen, bladder, ureter and urethra.

In another aspect, the invention features a method for producing an artificial bladder construct comprising:

providing a biocompatible substrate in the shape of a bladder;

creating a first cultured polylayer comprising a smooth muscle cell population on one area of the biocompatible substrate, wherein the first polylayer is attached to the biocompatible substrate;

creating a second cultured polylayer comprising a urothelial cell population, wherein the second polylayer is coupled to the first polylayer by a chimeric interface, such that the construct provides the functional equivalent of a natural bladder upon implantation, thereby producing an artificial bladder construct.

In a preferred embodiment, the chimeric interface further comprises an interstitial is submucosa produced by at least one of the polylayers.

In another aspect, the invention features a method for treating a subject with a genitourinary disorder comprising:

providing an artificial organ construct having a first cultured polylayer of a smooth muscle cell population, and second cultured polylayer of a urothelial cell population, wherein the second polylayer is coupled to the first polylayer by a chimeric interface;

implanting the organ construct into the subject, such that the construct provides the functional equivalent of a natural structure; and monitoring the subject for a modulation in the genitourinary disorder.

DETAILED DESCRIPTION

So that the invention may more readily be understood, certain terms are first defined.

The term "polylayer" as used herein refers to an arrangement comprising multiple layers of a homogenous cultured cell population layered over each other. The process of producing a "polylayer" involves depositing one layer of a cell population on a surface, e.g., a biocompatible substrate. The deposited cells are cultured in growth medium until they develop and proliferate to produce a first monolayer comprising cells with a desired phenotype and morphology. Once the first monolayer has attained a desired cell density, a second layer of the same cell population is depositing on the first monolayer. The second layer of deposited cells are cultured in growth medium which supplies nutrients to both the second cell layer and the first monolayer, until the cells in the second layer develop and proliferate to a desired cell density to produce a bilayer having cells with a desired phenotype and morphology. A third layer of same cell population is deposited on the bilayer, and the cells are cultured in growth medium which supplies nutrients to the bilayer and the cells of the third layer, until the cells of the third layer develop and proliferate to a desired density to produce a trilayer with a desired phenotype and morphology. The process is repeated until a polylayer comprising many layers of a homogenous cell population is produced. The characteristics of the polylayer is such that it closely resemble the morphology and functional characteristics of the equivalent parenchyma tissue of an in vivo organ. For example, a polylayer comprising a smooth muscle cell population may have functional characteristics of the smooth muscle tissue of a bladder, i.e., the detrusor.

The term "coupled" as used herein refers to the mutual intimate interactions between two different cell populations in contact with each other. These mutual interaction involve cell-cell interaction, growth, development, and proliferation. The cellular behavior responsible for the development, repair and maintenance of tissues is regulated, largely, by interactions between cells and components of their microenvironment. These interactions are mediated by cell surface molecules that bind, growth factors, enzymes, and other molecules that induce responses which result in changes of cellular phenotype. These interactions also result in the generation of new cells, which may be capable of generating cellular material with unique functional properties that is different from the functional properties of the each of the different cell populations.

The term "chimeric interface" as used herein refers to the boundary formed between two different cell populations.

The term "functional equivalent" as used herein refers to a structure, e.g., an artificial organ produced by the method of the invention that behaves in the same, or similar manner as a natural organ, for example, the artificial bladder has the same functional characteristics as an in vivo bladder.

The term "interstitial biomaterial" as used herein refers to the formation of cellular material at the chimeric interface where two different cell populations are in mutual contact with each other. The term "interstitial biomaterial" in its broadest concept is intended to include the formation of any new cellular material formed when two or more different cell is populations are in contact with each other. The new cellular material resembles the equivalent cellular material produced in normal in vivo cellular development of the organ. For example, in the reconstruction of an artificial bladder, the two different cell populations in mutual contact with each other are the smooth muscle cell population, and the urothelial cell population. The "interstitial biomaterial" produced at the interface of these two populations would therefore resemble that of the submucosa.

The phrase "genitourinary disorder" as used herein refers to a disease or infection that affect the normal function of the bladder, ureter and urethra.

The term "subject" as used herein is intended to include living organisms in which an immune response is elicited. Preferred subjects are mammals. Examples of subjects include but are not limited to, humans, monkeys, dogs, cats, mice, rats, cows, horses, pigs, goats and sheep.

The term "biocompatible substrate" as used herein refers to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired organ that requires replacing. The polymer can also be shaped into a part of an organ that requires replacing.

In another embodiment, the biocompatible substrate is a decellularized structure. The term "decellularized structure" as used herein refers to a three-dimensional biological arrangement, (e.g., an organ), produced by a process in which the entire cellular and tissue content is removed, leaving behind a complex infra-structure. Organs such as the bladder, or the kidney are composed of various specialized tissues. The specialized tissue structures of an organ is the parenchyma which provides the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The term "decellularized structure" is intended to include whole organs from which the cellular and tissue material is removed. The term "decellularized structure" is also intended to include parts of an organ structure, e.g., the renal artery of a kidney, from which cellular and tissue material has been removed. The decellularized structure provides a biocompatible substrate onto which different cell populations can be infused. Decellularized structures can be rigid, or semi-rigid, having an ability to alter their shapes. For example, a decellularized bladder is capable of distending when filled with fluid, but returns back to its original shape once the fluid has been removed. Examples of decellularized organs include, but are not limited to, the heart, kidney, liver, pancreas, spleen, bladder, ureter and urethra.

The present invention describes compositions and methods for in vitro organ reconstruction. Generally, the invention features multicellular organs comprising at least two different cell populations. The organ constructs comprise a first cultured polylayer of cells derived from a first cell population, and a second cultured polylayer of cells derived from a second cell population that is different from the first cell population, wherein the second polylayer is coupled to the first polylayer by a chimeric interface to produce a construct that is the functional equivalent of a natural biological structure.

The invention also features methods for producing artificial organs using a biocompatible substrate in the shape of an organ, by creating a first cultured polylayer of cells derived from a first cell population on one area of the biocompatible substrate, the first polylayer is attached to the biocompatible substrate;

creating a second cultured polylayer of cells derived from a second cell population that is different from the first cell population, the second polylayer is coupled to the first polylayer by a chimeric interface such that the construct provides the functional equivalent of a natural biological structure upon implantation, thereby producing an artificial organ construct.

Various aspects of the invention are described in further detail in the following subsections:

I. Culturing Cells for the Organ Reconstruction

One aspect of the invention pertains to artificial organ constructs comprising at least two different cell populations. The artificial constructs can be allogenic artificial constructs, where the different cell populations are derived from the subject's own tissue. For example, the cells can be derived from a human organ, such as, the bladder, urethra, ureter, and other urogenital tissue. The artificial organ construct can also be xenogenic, where the different cell populations are derived form a mammalian species that is different from the subject. For example the cells can be derived from organs of mammals such as humans, monkeys, dogs, cats, mice, rats, cows, horses, pigs, goats and sheep.

Cells can be isolated from a number of sources, for example, from biopsies, or autopsies. The isolated cells are preferably autologous cells, obtained by biopsy from the subject. For example, a biopsy of skeletal muscle from the arm, forearm, or lower extremities, or smooth muscle from the area treated with local anaesthetic with a small amount of lidocaine injected subcutaneously, and expanded in culture. The biopsy can be obtained using a biopsy needle, a rapid action needle which makes the procedure quick and simple. The small biopsy core of either skeletal or smooth muscle can then be expanded and cultured, as described by Atala, et al., (1992) *J. Urol.* 148, 658–62; Atala, et al. (1993) *J. Urol.* 150: 608–12 and in Example 1. Cells from relatives or other donors of the same species can also be used with appropriate immunosuppression.

Methods for the isolation and culture of cells are discussed in Fauza et al. (1998) *J. Ped. Surg.* 33, 7–12, incorporated herein by reference. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption can also be accomplished by a number of methods including, but not limited to, scraping the surface of the organ, the use of grinders, blenders, sieves, homogenizers, pressure cells, or insonicators. For a review of tissue disaggregation techniques, see Freshney, (1987), Culture of Animal Cells. A Manual of Basic Technique, 2d Ed., A. R. Liss, Inc., New York, Ch. 9, pp. 107–126.

Preferred cell types include, but are not limited to, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage. In some cases, it may also be desirable to include nerve cells. In a preferred embodiment, urothelial cells and smooth muscle cells are isolated. Urothelial cells and smooth muscle cells from all developmental stages, such as, fetal, neonatal, juvenile to adult may be used.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, (1987), Culture of Animal Cells. A Manual of Basic Techniques, 2d Ed., A. R. Liss, Inc., New York, Ch. 11 and 12, pp. 137–168. For example, urothelial cells may be enriched by fluorescence-activated cell sorting, and smooth muscle cells and fibroblast cells may be reduced for urothelial cell collection. Similarly, smooth muscle cells may be enriched and urothelial cells and fibroblast cells may be reduced for smooth muscle cell collection.

Cell fractionation may also be desirable, for example, when the donor has diseases such as bladder cancer or metastasis of other tumors to the bladder. A bladder cell population may be sorted to separate malignant bladder cells or other tumor cells from normal noncancerous bladder cells. The normal noncancerous bladder cells, isolated from one or more sorting techniques, may then be used for bladder reconstruction.

Isolated cells can be cultured in vitro to increase the number of cells available for coating the biocompatible substrate. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the biocompatible substrate.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Urothelial and muscle cells could be transfected with specific genes prior to coating the biocompatible substrate. The cell-substrate construct could carry genetic information required for the long term survival of the host or the artificial organ.

Isolated cells can be normal or genetically engineered to provide additional or normal function. Methods for genetically engineering cells with retroviral vectors, polyethylene glycol, or other methods known to those skilled in the art can be used. These include using expression vectors which transport and express nucleic acid molecules in the cells. (See Goeddel; *Gene Expression Technology: Methods in Enzymology* 185, Academic Press, San Diego, Calif. (1990).

Vector DNA is introduced into prokaryotic or cells via conventional transformation or transfection techniques. Suitable methods for transforming or transfecting host cells can be found in Sambrook et al. (*Molecular Cloning: A Laboratory Manual*, 2nd Edition, Cold Spring Harbor Laboratory press (1989)), and other laboratory textbooks.

II Organ Reconstruction

Another aspect of the invention pertains to methods of producing multilayered artificial organs. In a preferred embodiment, the artificial organ is produced on one surface of the biocompatible substrate. Building of three-dimensional artificial constructs in vitro, prior to implantation, facilitates the eventual terminal differentiation of the cells after implantation4in vivo, and minimizes the risk of an inflammatory response towards the biocompatible substrate-cellular matrix, thus avoiding graft contracture and shrinkage. The following sections describe examples of suitable biocompatible substrates.

(i) Decellularized Structures

Biostructures, e.g., whole organs, or parts of organs can be decellularized by removing the entire cellular and tissue content from the organ. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components an the nuclear components.

Preferably, the biostructure, e.g., an organ, is decellularized by removing the cell membrane and cellular debris surrounding the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ, agitating the organ, or stirring the organ in a suitable volume of fluid, e.g., distilled water. In one preferred embodiment, the gentle mechanical disruption method includes stirring the organ in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infrastructure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octyl α-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J. , U.S.A. and Judith Neugebauer, A Guide to the Properties and Uses of Detergents in Biology and Biochemistry, Calbiochem.R., Hoechst Celanese Corp., 1987. In one preferred embodiment, the non-ionic surfactant is the Triton. series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

(ii) Polymers

Polymers, such as polyglycolic acid are also suitable biocompatible structures for organ reconstruction. The biocompatible polymer may be shaped using methods such as, solvent casting, compression molding, filament drawing, meshing, leaching, weaving and coating.

In solvent casting, a solution of one or more polymers in an appropriate solvent, such as methylene chloride, is cast as a branching pattern relief structure. After solvent evaporation, a thin film is obtained.

In compression molding, a polymer is pressed at pressures up to 30,000 pounds per square inch into an appropriate pattern. Filament drawing involves drawing from the molten polymer and meshing involves forming a mesh by compressing fibers into a felt-like material.

In leaching, a solution containing two materials is spread into a shape close to the final form of the organ. Next a solvent is used to dissolve away one of the components, resulting in pore formation. (See Mikos, U.S. Pat. No. 5,514,378, hereby incorporated by reference).

In nucleation, thin films in the shape of the organ is exposed to radioactive fission products that create tracks of radiation damaged material. Next, the polycarbonate sheets are etched with acid or base, turning the tracks of radiation-damaged material into pores. Finally, a laser may be used to shape and burn individual holes through many materials to form an organ structure with uniform pore sizes.

The polymeric substrate can be fabricated to have a controlled pore structure that no allows nutrients from the culture medium to reach the deposited cell population, but prevent cultured cells from migrating through the pores. In vitro cell attachment and cell viability can be assessed using scanning electron microscopy, histology and quantitative assessment with radioisotopes.

The polymeric substrates can be shaped into any number of desirable configurations to satisfy any number of overall system, geometry or space restrictions. For example, in using a polymeric substrate for bladder reconstruction, the substrate may be shaped to conform to the dimensions and shapes of the whole, or a part of a bladder. The polymeric substrates can be shaped to different sizes to conform to the bladders of different sized patients. The polymeric substrate may also be shaped to facilitate special needs of a patient, for example, a disabled patient, who may have a different abdominal cavity space may require a bladder reconstructed to adapt to fit the space.

In other embodiments, the polymeric substrate is used for the treatment of laminar structures in the body such as urethra, vas deferens, fallopian tubes, lacrimal ducts. In those applications the polymeric substrate can be shaped as a hollow tube.

A biocompatible substrate (decellularized organ or a polymer) can be permeated with a material, for example liquified copolymers (poly-DL-lactide co-glycolide 50:50 80 mg/ml methylene chloride) to alter its mechanical properties. This can be performed by coating one layer, or multiple layers until the desired mechanical properties are achieved.

III Generation of a Polylayer of a Cell Population

In another aspect, the invention features methods of making artificial organs using cultured cell populations used to create polylayers of the artificial multicellular organ construct. Cells can be expanded as described in Section I, and used to create polylayers on one side of a biocompatible substrate.

a) Production of Polylayers on a Decullularized Structure

In one embodiment, different cultured cell populations can be used to produce different polylayers on a decellularized structure, for example a decellularized organ, or a part of an organ. A first homogenous cell suspension can be perfused into the decellularized structure using needles embedded within localized positions of the three-dimensional infra-structure of the decellularized organ. The perfused cells distribute between the three-dimensional interstices of the infra-structure and grow to produce a layer of cells that envelopes the infra-structure. After perfusion of the first homogenous cell suspension, the decellularized organ is incubated in culture medium at 37° C. until the cells develop and proliferate to produce a monolayer of a first population of cultured cells that is attached to the infra-structure of the decellularized organ. Once the monolayer is established, the first homogenous cell suspension is again perfused into the decellularized structure over the monolayer. The decellularized organ is incubated until the cells develop and proliferate to produce a second monolayer of cells over the first monolayer, thereby producing a bilayer. The process is repeated until a polylayer of a first homogenous cell population is produced.

The first polylayer resembles the functional characteristics and morphology of the equivalent parenchyma tissue of an in vivo organ. For example, with a decellularized bladder, the first cell population is a smooth muscle cell population. The smooth muscle cell suspension is perfused into the bladder until a polylayer of smooth muscle tissue is formed, which has the functional characteristics that resemble smooth muscle tissue (i.e. the detrusor) of a bladder.

After creating the first polylayer, a second polylayer is created using a second cultured cell population that is different form the first cell population. A cell suspension of the second homogenous cell population is perfused onto the first polylayer in the decullularized organ. The perfused cells distribute along the first polylayer, and the decullularized organ is incubated until the cells of the second cell population develop and proliferate into a first monolayer. Once the first monolayer is established, the second homogenous cell population is again perfused into the decellularized structure over the first monolayer. The decellularized organ is incubated until the cells develop and proliferate to produce a second monolayer over the first monolayer thereby producing a bilayer. The process is repeated until a second polylayer of a second homogenous cell population is produced.

The second polylayer resembles the functional and morphological characteristics of the equivalent parenchyma tissue of an in vivo organ. For example, the second polylayer for the bladder construct is a urothelial polylayer which resembles the morphological and functional characteristics of the urothelial tissue (i.e., the mucosa) of the bladder.

The skilled artisan will appreciate that a number of heterogenous polylayers can be produced to create artificial multicellular organs constructs. Each polylayer comprises multiple layers of a homogenous cell population, although the cell populations of the polylayers are different. In one embodiment, the artificial organ comprises at least about five polylayers. In another embodiment, the artificial organ comprises at least about four polylayers. In yet another embodiment, the artificial organ comprises at least about three polylayers. In a preferred embodiment, the artificial organ comprises at least about two polylayers.

A chimeric interface is produced where two or more heterogenous polylayers are in mutual contact with each other. This enables unhindered interaction to occur between the cells of the polylayers. Extensive interactions between different cell populations results in the production of a interstitial biomaterial which is different from each of the polylayers. As the interaction between the two different cell populations is not hindered by structural barriers such as, biocompatible substrates (e.g. polymers), the cells at the chimeric interface resume a more natural shape and configuration. By providing a microenvironment at the chimeric interface that is more conducive to the microenvironment of an in vivo organ, the cells at the chimeric interface develop more naturally and produce growth factors and other proteins which promote normal division and differentiation. This can result in the production of interstitial biomaterial that provides unique biological and functional properties to create artificial organs that more closely resemble those found in the in vivo. For example, interaction of the smooth muscle polylayer and the urothelial polylayer of an artificial bladder construct produces a chimeric interface resulting in the production of a layer of cells that resembles the submucosa of an in vivo bladder. The submucosa provides functional characteristics that are unique from those of the smooth muscle cells and the urothelial cells, in that the submucosa when fully developed provide a blood supply to the smooth muscle cells.

The skilled artisan will appreciate that any interstitial biomaterial produced when two or more heterogenous polylayers comprising different cell populations interact, is within the scope of the invention. The different interstitial biomaterial produced will depend on the type of cells in the heterogenous polylayer.

In one embodiments, additional collagenous layers may be added to the inner surfaces of the decellularized structure to create a smooth surface as described in International PCT Publication No. WO 95/22301, the contents of which are incorporated herein by reference. This smooth collagenous layer promotes cell attachment which facilitates growth and development. As described in International PCT Publication No WO 95/22301, this smooth collagenous layer may be made from acid-extracted fibrillar or non-fibrillar collagen, which is predominantly type I collagen, but may also include type II collagen, type IV collagen, or both. The collagen used may be derived from any number of mammalian sources, typically pig and cow skin and tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949 issued to Kemp et al., incorporated herein by reference.

In another embodiment, additional collagenous layers may be added between the heterogenous polylayers to promote growth and development between the cells of heterogeneous polylayers. In yet another embodiment, factors such as nutrients, growth factors, cytokines, extracellular matrix components, inducers of differentiation or products of secretion, immunomodulation, biologically active compounds which enhance or allow growth of the cellular network or nerve fibers can be added between the heterogenous polylayers (see Section IV).

b) Production of Polylayers on a Polymer

In another embodiment, different cultured cell populations can be used to produce heterogenous polylayers on one area of a polymer. Examples of suitable polymers include, but are not limited to, collagen, poly(alpha esters) such as poly(lactate acid), poly(glycolic acid), polyorthoesters and polyanhydrides and their copolymers, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials.

In a preferred embodiment, one side of the biocompatible substrate is used to create a polylayer of a first homogenous cell population. This is performed by coating one side of the biocompatible substrate with a suspension of a first homogenous cell population, e.g., smooth muscle cells. The first homogenous cell suspension is incubated in culture medium until the cells develop and proliferate to produce a monolayer and cells of the monolayer attach to the biocompatible substrate. Once the monolayer is established, the first homogenous cell suspension is deposited over the first monolayer, and the cells are cultured until they develop and proliferate to produce second monolayer of cells over the first monolayer, thereby producing a bilayer. The process is repeated until a polylayer comprising multiple layers of the first homogenous cell population is generated. The first polylayer has morphological and functional characteristics that resemble the parenchyma tissue of an in vivo organ e.g., the detrusor.

After the first polylayer is established, a second polylayer comprising a second homogenous cell population is created, (e.g., urothelical cell population) over the first polylayer. This produces a chimeric interface between the two different cell populations. The second polylayer is created by depositing a cell suspension of a second homogenous cell population onto the first polylayer. The cells of second homogenous cell population are cultured until they develop and proliferate to produce a first monolayer. Once the first monolayer is established, the second homogenous cell suspension is deposited over the first monolayer, and the cells are cultured until they develop and proliferate to produce a second monolayer of cells over the first monolayer, thereby producing a bilayer. The process is repeated until a second polylayer comprising multiple layers of a second homogenous cell population is generated. The second polylayer has morphological and functional characteristics that resembles the parenchyma tissue of an in vivo organ e.g., the mucosa. An interstitial biomaterial is produced at the chimeric interface between the two different cell populations, as described above.

The invention therefore provides compositions and methods of producing artificial organs with a multicellular organization that more closely resemble that of a native in vivo organ. The cellular organization includes heterogenous polylayers. Each polylayer of the artificial organ comprises multiple layers of a homogenous cell population, generating an organized structure with a cellular morphology and functional characteristics that resemble the equivalent tissue native in vivo layers of a natural organ.

The chimeric interface between the different polylayers provides a microenvironment that mimics the native microenvironment between different cell populations. The skilled artisan will appreciate that cell shape plays an important role in cell division and differentiation (see e.g., Damell et al. Molecular Cell Biology (1986) published by Scientific American Books). The more natural microenvironment created by the method of the invention, permits mutual, dynamic, unhindered cell-cell interactions between cells of the heterogenous polylayers. These unhindered interactions enable the cells at the interface to resume a more natural cellular and morphological configuration. The more natural cell development at the chimeric interface enables the cells to produce proteins which promote normal division and differentiation.

The artificial organ construct of the invention, functioning as a substitute body part, can be flat, tubular, or of complex geometry. The shape of the organ will be decided by its intended use. The artificial organ can be implanted to repair, augment, or replace diseased or damaged organs, such as abdominal wall defects, pericardium, hernias, and various other organs and structures including, but not limited to, bone, periosteum, perichondrium, intervertebral disc, articular cartilage, dermis, epidermis bowel, ligaments, and tendons. In addition, the tissue repair fabric can be used as a vascular or intra-cardiac patch, or as a replacement heart valve.

Flat sheets may be used, for example, to support prolapsed or hypermobile organs by using the sheet as a sling for the organs. This sling can support organs such as bladder or uterus.

Tubular grafts may be used, for example, to replace cross sections of tubular organs such as esophagus, trachea, intestine, and fallopian tubes. These organs have a basic tubular shape with an outer surface and luminal surface.

IV Cell Adhesion

In some embodiments, attachment of the cells to the biocompatible substrate is enhanced by coating the biocompatible substrate with compounds such as basement membrane components, agar, agarose, gelatin, gum arabic, collagens types I, II, III, IV, and V, fibronectin, laminin, glycosaminoglycans, mixtures thereof, and other hydrophilic and peptide attachment materials known to those skilled in the art of cell culture. A preferred material for coating the biocompatible substrate is collagen.

In other embodiments, biocompatible substrates can be treated with factors or drugs prior to implantation, before or after the biocompatible substrate is coated with cultured cells, e.g., to promote the formation of new tissue after implantation. Factors including drugs, can be incorporated into the biocompatible substrate or be provided in conjunction with the biocompatible substrate. Such factors will in general be selected according to the tissue or organ being reconstructed or augmented, to ensure that appropriate new tissue is formed in the engrafted organ or tissue (for examples of such additives for use in promoting bone healing, (see, e.g., Kirker-Head, (1995) *Vet. Surg.* 24: 408–19). For example, when biocompatible substrates are used to augment vascular tissue, vascular endothelial growth factor (VEGF), can be employed to promote the formation of new vascular tissue (see, e.g., U.S. Pat. No. 5,654,273 issued to Gallo et al.). Other useful additives include antibacterial agents such as antibiotics.

Grafting of artificial organs can be performed according to art-recognized methods (see e.g., Fauza et al. (1998) *J. Ped. Surg.* 33, 7–12).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Cell Harvesting and Culturing

The harvested cells were cultured according to previously published protocols of Atala et al., (1993) *J. Urol.* 150: 608, Cilento et al., (1994) *J. Urol.* 152: 655, Fauza et to al., (1998) *J. Ped. Surg,* 33, 7–12, which are herein specifically incorporated by reference.
a) Culturing Urothelial Cell Populations A bladder specimen was obtained and prepared for culturing. To minimize cellular injury, the specimen was sharply excised rather than cut with an elecrocautery. The serosal surface was marked with a suture to ensure there will be no ambiguity as to which side represented the urothelial surface.

The specimen was processed in laminar flow cell culture hood, using sterile instruments. Culture medium with Keratinocyte-SFM (GIBCO BRL (Cat. No. 17005), with Bovine Pituitary Extract (Cat. No. 13028, 25 mg/500 ml medium) and Recombinant Epidermal Growth Factor (Cat. No. 13029, 2.5 $\mu$g/500 ml medium) as supplement was prepared. 10 ml of culture medium at 4° C., was placed in each of two 10 cm cell culture dishes, and 3.5 ml in a third dish. Blood was removed from the specimen by placing the specimen in the first dish and gently agitating it back and forth. The process was repeated in the second dish, and finally the specimen was transferred to the third dish. The urothelial surface was gently scraped with a No. 10 scalpel blade without cutting into the specimen. The urothelial cells were visible as tiny opaque material dispersing into the medium. The urothelial cell/medium suspension was aspirated and seeded into six wells of a 24-well cell culture plate with approximately 0.5 to 1 ml of medium to each well to give a total of 1 to 1.5 ml per well. The cells were incubated at 37° C. with 5% $CO_2$.

The following day (Day 1 post harvesting), the medium was aspirated from the six wells and fresh medium applied. The cells were centrifuged at 1000 rpm for 4 minutes and the supernatant was removed. The cells were resuspended in 3 to 4.5 ml of fresh medium warmed to 37° C. in a 24-well plate.

The culture medium was removed and PBS/EDTA (37° C., pH 7.2, 0.53 mM EDTA (0.53 ml of 0.5M EDTA, pH 8.0, in each 500 ml of PBS)), was added to each 24-well plate well, or 10 ml to each 10 cm dish. The cells were then passaged in two 10 cm dishes. Hereafter the cells were passaged whenever they reached 80 to 90% confluence, without allowing the cells to reach 100% confluence.

The cells were observed under a phase contrast microscope. When the cell-cell junctions were separated for the majority of the cells (approximately 5 to 15 minutes), the PBS/EDTA was removed and 300 $\mu$l Trypsin/EDTA (37° C., GIBCO BRL, Cat. No. 25300-054), was added to each 24-well plate well or, 7 ml to each 10 cm dish. The plate/dish was periodically agitated. When 80 to 90% of the cells detached from the plate and started to float (approximately 3 to 10 minutes), the action of the Trypsin was inhibited by adding 30 $\mu$l soy bean Trypsin inhibitor (GIBCO BRL, Cat. No. 17075-029, 294 mg of inhibitor to 20 ml PBS), to each 24-well place well or 700 $\mu$l to each 10 cm dish to stop the action of the EDTA. 0.5 ml culture medium was added to each 24-well plate well or 3 ml culture medium was added to each 10 cm dish. The PBS/EDTA and Trypsin/EDTA incubations were performed at room temperature, but were more effective if the plates were incubated at 37° C.

The cells were harvested by centrifugation at 1000 rpm for 4 minutes, and the supernatant removed. The cells were resuspended in 5 ml culture medium, and the number of cells was determined using a hemocytometer. Cell viability was determined by the standard Trypan blue stain test. The optimal seeding density for a 100 mm culture plate was approximately $1 \times 10^6$ cells/plate. The desired number of cells was aliquoted into the dish and the volume of a medium was added to a total of approximately 10 ml/plate.
b) Culturing Bladder Smooth Muscle Cells.

After removing the urothelial cell layer from the bladder specimen as described in Example I, section (a), the remaining muscle was dissected into 2–3 mm muscle segments. Each muscle segment was spaced evenly onto a 100 mm cell culture dish. The muscle segments were dried and allowed to adhere to the dish (approximately 10 minutes). 20 ml of Dulbecco's Modified Eagle Media with 10% FCS was added to the dried muscle segments. The muscle segments were incubated for 5 days undisturbed at 37° C. with 5% $CO_2$. The culture media was changed on the 6th day and any non-adherent segments were removed. The remaining segments were cultured for a total of 10 days, after which all the muscle segments were removed. The cells from the muscle segments that had adhered to the dish were incubated until small islands of cells appeared. These cells were trypsinized, counted and seeded into a T75 culture flask.

The cells were fed every 3 days depending on the cell density, and the cells were passaged when they reached 80–90% confluence.

Example 2

Bladder Augmentation Using Fetal Tissue

The following Example demonstrates the feasibility of producing functional multicellular artificial organs using urothelial and smooth bladder cells from fetal bladder, as described by Fauza et al. (1998) *J. Ped. Surg.* 33, 7–12.
Maternal and Fetal Surgical Manipulation Time-dated pregnant ewes at 90 to 95 days gestation were anesthetized with 2% to 4% halothane (Halocarbon Laboratories, River Edge, N.J.), after induction with 15 mg/kg of ketamine (Parke-Davis Co., Morris Plains, N.J.) intramuscularly. They received 1 g of cefazolin (BMH Ltd., Philadelphia, Pa.) intravenously. Ten fetal lambs underwent open surgical creation of a bladder exstrophy defect by marsupializing the anterior portion of the bladder to the abdominal wall. At the end of the procedure, the amniotic fluid, which had been previously removed and kept at 37° C., was reinfused into the amniotic cavity, together with 500 mg of cefazolin. The gestational membranes and uterine wall were closed in one layer with a TA 90 mm titanium surgical stapler (United States Surgical Corp. (USSC), Norwalk, Conn.). Subsequently, the fetuses were divided in two groups.

In group 1, videofetoscopic access to the amniotic cavity was established as described by Fauza et al. (1998) *J. Ped. Surg.* 33, 7–12. Semiflexible, balloon-tipped cannulas (Marlow Surgical Technologies, Inc., Willoughby, Ohio) were introduced in the uterus through three ports (one of 10 mm and two of 5 mm in size). Videofetoscopic manipulation was performed either under continuous warmed saline amnioinfusion, or with medical air as working media. A full-thickness specimen no larger than 1.5×1.0 cm was harvested from the exstrophic bladder. A 30° 5-mm telescope (Karl Storz Endoscopy-America, Inc., Los Angeles, Calif.), along with 2-mm and 5-mm endoscopic graspers, 2-mm and 5-mm endoscopic shears, and 10-mm titanium endoscopic clips, the latter for closure of the harvested area, were used (all from USSC). The uterine ports were closed with 4-0 synthetic absorbable Glycomer 631 (Biosyn; USSC) in double-running fashion. In group II, no further fetal procedures were performed.

The mother's abdomen was closed in layers. On the first postoperative day, the ewes received 1.2 million units of benzatin penicillin intramuscularly (Wyeth Laboratories, Inc., Philadelphia, Pa.). Normal delivery was allowed.

Cell Manipulation

The urothelial and muscular layers of the fetal bladder specimens harvested were surgically detached from each other and processed separately.

Cell Culture.

Bladder cells were cultured by previously described methods (Cilento, et al (1994) *J. Urol.*, 52:665–670) and as described in Example 1. Briefly, detrusor muscle cells were isolated by cutting the smooth muscle specimens into fragments of approximately 0.5 mm in diameter. The explants were plated on a 10-cm culture dish and maintained and expanded with Dulbecco's Modified Eagles Medium (DMEM, Sigma Chemical Co., St. Louis, Mo.) supplemented with 10% fetal calf serum (Biowhittaker, Inc., Walkersville, Md.) in a 95% humidified, 5.0% $CO_2$ chamber at 37° C., as described in detail in Example I.

Urothelial cells were separated from the surgical specimen through curettage of its epithelial surface and placed on a 24-well plate. They were maintained and expanded with serum-free keratinocyte growth medium containing 5 ng/mL of epidermal growth factor and 50 μg/mL of bovine pituitary extract (Keratinocyte SFM, Gibco BRL, Life Technologies, Grand Island, N.Y.) in the same chamber described above.

Both detrusor muscle and urothelial cells were independently expanded in vitro for 50 to 55 days, until reaching an approximate density of $1.3 \times 10^7$ cells/cm².

Cell Delivery.

The cell delivery vehicle consisted of unwoven sheets of polyglycolic acid polymer with a density of 58 mg/mL and a fiber diameter of 15 μm. The mesh had a greater than 95% porosity before seeding and was sterilized by ethylene oxide. The scaffold was designed to degrade via hydrolysis within 6 to 8 weeks after implantation.

Seven to 10 days before implantation in vivo, the detrusor muscle cells were seeded on a 16- to 20-cm$^2$, 3-mm thick polyglycolic acid polymer scaffold. Three days later, the urothelial cells were seeded on the same polymer, over the detrusor cells. The average number of cells per polymer was 200 million. The urothelial/detrusor cells bilayer was left in culture in DMEM for approximately 1 week until implantation on the newborn animals.

Neonatal Manipulation

Sulfamethoxazole/trimethoprim (Barre-National, Inc., Baltimore, Md.) (6 mg/kg of sulfa) was given to all newborns orally once daily for prophylaxis.

Surgery.

One to 4 days after birth, the newborns were anesthesized with 1.5% to 3.5% Isoflurane (Abbott Laboratories, North Chicago, Ill.), after induction with 15 mg/kg of ketamine intramuscularly. One dose of 100 mg/kg of cefazolin was given intravenously. The exstrophic bladder was surgically detached from the abdominal wall. Bladder reconstruction was performed in each group, as follows.

In group I, the autologous engineered fetal bladder tissue was used for surgical augmentation of the bladder. The borders of the engineered tissue were sutured to the native bladder edges with 3-0 synthetic absorbable lactomer 9-1 (Polysorb; USSC) in a running fashion, so that the urothelial cell layer was on the luminal portion of the bladder and the muscular layer on its outer portion. Fibrin glue (Melville Biologics, Inc., New York, N.Y.) was applied on the external surface of the engineered tissue after its implantation. Omentum was used to cover the engineered tissue—it was loosely attached to the bladder, around the edges of the implant, with four simple cardinal stitches of 3-0 synthetic absorbable Lactomer 9-1. In group II, the bladder defect was closed primarily, with 3-0 synthetic absorbable Lactomer 9-1 in a running fashion.

In both groups, during either of the above-mentioned reconstruction techniques, a 5F, 15-in. long multiperforated plastic catheter (Davol Inc., Cranston, R.I.) was left inside the bladder, exteriorized through a separate stab wound and placed to drain continuously into an open external reservoir. On the first postoperative day, all newborns received one dose of 0.6 mU of benzatin penicillin intramuscularly.

Follow-up.

Three weeks post-operatively a contrast cystogram was performed in both groups with diluted iothalamate meglumine (Mallinck-rodt Medical, Inc., St. Louis, Mo.) instilled at 15 mm Hg through the bladder catheter. The catheter was then removed. Sulfamethoxazole/trimethoprim administration was discontinued after catheter (Medex Inc., Hilliard, Ohio) was directly inserted into the bladder and connected to a 78534C digital monitor/terminal (Hewlett Packard, Andover, Mass.). After the bladder was completely emptied. Normal saline was infused at a rate of 8 mL/min. At each 5 mL infusion, bladder pressure was recorded after stabilization. This was followed by a radiographic cystogram. Animals were killed by intravenous injection of Somlethal (J.A. Webster, Inc., Sterling, Mass.). The bladder was removed for histological analysis.

Histological Analysis

Specimens of primarily closed and engineered bladder were immersed in 10% buffered formalin solution (Stephens Scientific, Riversdale, N.J.) on retrieval and submitted to regular hematoxilin-eosin processing 24 to 48 hours post-harvesting. Microscopic analysis was performed at 25× and 100× magnification using a Zeiss (Zeiss, Germany) laboratory light microscope.

Statistical Analysis

Statistical Analysis was performed by analysis of variance (ANOVA) and the Scheffe-f test at 95% confidence limit. P values of less than 0.05 were considered significant.

Results

Contrast cystograms were evidently different in both groups. The engineered bladders produced images close to normal, as opposed to smaller and distorted ones observed in the group undergoing primary bladder closure.

At 2 months of age, the engineered bladders were more compliant (P<0.05) and had greater capacity at pressures higher than 30 mm Hg (P<0.05) than those closed primarily.

Histological analysis of the engineered tissue showed a multilayered, pseudostratified urothelial lining (transitional epithelium) on its luminal side and overlying layers of smooth muscle cells surrounded by connective tissue. The microscopic architecture of the engineered mucosa was distinct from, but resembled that, of native bladder. Muscular hypertrophy was present in the exstrophic bladders primarily closed, as expected, but not in the engineered ones.

The method of the invention produces autologous bladder tissue, and also overcomes certain limitations of autologous transplantation. After fetal harvest, the interval needed to engineer an autologous graft is parallel to the remainder of gestation, therefore time is not a limiting factor. Moreover, there is frequently an inverse relationship between donor age and cell growth rate in culture (Langer, et al. (1993) *Science*, 260:920–926). The fact that fetal cells were used in our experiment maximized this principle, as demonstrated by the high expansion rate observed with the fetal detrusor cells.

In addition, bladder augmentation through the method of the invention hereby presented can prove useful for the treatment of certain human congenital anomalies such as bladder and cloacal exstrophies, in which there may not be enough residual bladder for proper closure during the neonatal period.

What is claimed is:

1. An artificial organ construct comprising:
   a biocompatible substrate;
   a first cultured polylayer of cells derived from an isolated population of smooth muscle cells on the biocompatible substrate; and
   a second cultured polylayer of cells derived from a second cell population that is different from the smooth muscle cell population, wherein the second polylayer is coupled to the first polylayer at a boundary between the first and second polylayer such that the construct provides the functional equivalent of a natural biological structure upon implantation.

2. The artificial organ of claim 1, further comprising a third cultured polylayer of cells derived from a third cell population that is different from the smooth muscle cell population and the second cell population, wherein the third polylayer is coupled to the second polylayer at a boundary between the second and third polylayer.

3. The artificial organ of claims 1 or 2, wherein the at a boundary between the polylayers further comprises an interstitial biomaterial produced by at least one of the polylayers.

4. The artificial organ of claim 3, wherein the interstitial biomaterial comprises cells with a normal morphology.

5. The artificial organ of claim 1, further comprising layering factors between the first and second polylayers, wherein the factors are selected from the group consisting of nutrients, growth factors, cytokines, extracellular matrix components, inducers of differentiation, products of secretion, immunomodulators, and biologically-active compounds which enhance or allow growth of the cellular network or nerve fibers.

6. The artificial organ of claim 1, wherein the organ is selected from the group consisting of heart, kidney, liver, pancreas, spleen, bladder, ureter and urethra.

7. The artificial organ of claim 1, wherein the artificial organ is a part of an organ selected from the group consisting of heart, kidney, liver, pancreas, spleen, bladder, ureter and urethra.

8. An artificial bladder construct comprising:
   a biocompatible substrate;
   a first cultured polylayer of cells derived from an isolated population of smooth muscle cells on the biocompatible substrate; and
   a second cultured polylayer of cells derived from a urothelial cell population, wherein the second polylayer is coupled to the first polylayer at a boundary between the first and second polylayer such that the construct provides the functional equivalent of a natural bladder upon implantation.

9. The artificial bladder of claim 8, wherein the boundary between the first and second polylayer further comprises an interstitial submucosa produced by at least one of the polylayers.

10. A method for producing an artificial organ construct comprising:
    providing a biocompatible substrate in the shape of an organ;
    creating a first cultured polylayer of cells derived from an isolated population of smooth muscle cells on the biocompatible substrate, wherein the first polylayer is attached to the biocompatible substrate; and
    creating a second cultured polylayer of cells derived from a second cell population that is different from the smooth muscle cell population, wherein the second polylayer is coupled to the first polylayer at a boundary between the first and second polylayer such that the construct provides the functional equivalent of a natural biological structure upon implantation, thereby producing an artificial organ construct.

11. The method of claim 10, further comprising creating a third cultured polylayer of cells derived from a third cell population that is different from the smooth muscle cell population and the second cell population, wherein the third polylayer is coupled to the second polylayer at a boundary between the second and third polylayer.

12. The method of claims 10 or 11, wherein the boundary between the polylayers further comprises an interstitial biomaterial produced by at least one of the polylayers.

13. The method of claim 12, wherein the interstitial biomaterial comprises cells with a normal morphology.

14. The method of claim 10 further comprising layering factors between the first and second polylayers, wherein the factors are selected from the group consisting of nutrients, growth factors, cytokines, extracellular matrix components, inducers of differentiation, products of secretion, immunomodulators, and biologically-active compounds which enhance or allow growth of the cellular network or nerve fibers.

15. The method of claim 10, wherein the artificial organ is selected from the group consisting of heart, kidney, liver, pancreas, spleen, bladder, ureter and urethra.

16. The method of claim 10, wherein the artificial organ is a part of an organ selected from the group consisting of heart, kidney, liver, pancreas, spleen, bladder, ureter and urethra.

17. The method of claim 10, wherein the biocompatible substrate is a polymer.

18. The method of claim 10, wherein the biocompatable substrate is a decellularized organ produced by removing cellular content from the organ leaving a three-dimensional scaffold of connective tissue.

19. The method of claim 18, wherein the decellularized organ is selected from the group consisting of heart, kidney, liver, pancreas, spleen, bladder, ureter and urethra.

20. The method of claim 18, wherein the decellularized organ is a part of a decellularized organ selected from the group consisting of heart, kidney, liver, pancreas, spleen, bladder, ureter and urethra.

21. A method for producing an artificial bladder construct comprising:

provinding a biocompatable substrate in the shape of a bladder;

creating a first cultured polylayer derived from an isolated population of smooth muscle cells on the biocompatable substrate, wherein the first polylayer is attached to the biocompatable substrate; and creating a second cultured polylayer comprising a urothelial cell population, wherein the second polylayer is coupled to the first polylayer at a boundary between the first and second polylayer, such that the construct provides the functional equivalent of a natural bladder upon implantation, thereby producing an artificial bladder construct.

22. The method of claim 21, wherein the boundary between the first and second polylayer further comprises an interstitial submucosa produced by at least one of the polylayers.

23. The method of claim 21, wherein the biocompatible substrate is a polymer.

24. The method of claim 21, wherein the biocompatable substrate is a decellularized bladder produced by removing cellular content from a mammalian bladder leaving a three-dimensional scaffold of connective tissue.

25. The method of claim 21, wherein the biocompatible substrate is a part of a decellularized bladder.

26. A method for treating a subject with a genitourinary disorder comprising:

providing an artificial organ construct having a first cultured polylayer of cells derived from an isolated population of smooth muscle cells on a biocompatable substrate, and second cultured polylayer of a urothelial cell population, wherein the second polylayer is coupled to the first polylayer at a boundary between the first and second polylayer;

implanting the organ construct into the subject, such that the construct provides the functional equivalent of a natural structure; and monitoring the subject for a modulation in the genitourinary disorder.

27. The method of claim 26, wherein the boundary between the first and second polylayer further comprises an interstitial submucosa produced by at least one of the polylayers.

28. The method of claim 26, wherein the biocompatable substrate is a polymer.

29. The method of claim 26, wherein the biocompatable substrate is a decellularized organ produced by removing cellular content from the organ leaving a three-dimensional scaffold of connective tissue.

30. The method of claim 29, wherein the decellularized organ is selected from the group consisting of bladder, ureter and urethra.

31. The method of claim 29, wherein the decellularized organ is a part of a decellularized organ selected from the group consisting of bladder, ureter and urethra.

* * * * *